(12) United States Patent
Raj et al.

(10) Patent No.: US 12,180,249 B1
(45) Date of Patent: Dec. 31, 2024

(54) COMPOSITIONS AND METHODS FOR SELECTIVE LABELING OF SECONDARY AMINES

(71) Applicant: Emory University, Atlanta, GA (US)

(72) Inventors: Monika Raj, Atlanta, GA (US); Ogonna Nwajiobi, Decatur, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 17/933,963

(22) Filed: Sep. 21, 2022

Related U.S. Application Data

(60) Provisional application No. 63/246,517, filed on Sep. 21, 2021.

(51) Int. Cl.
| | |
|---|---|
| *C07K 1/10* | (2006.01) |
| *C07D 233/88* | (2006.01) |
| *C07K 1/107* | (2006.01) |
| *C07K 1/22* | (2006.01) |

(52) U.S. Cl.
CPC .......... *C07K 1/1077* (2013.01); *C07D 233/88* (2013.01); *C07K 1/22* (2013.01)

(58) Field of Classification Search
CPC ....... C07K 1/1077; C07K 1/22; C07D 233/88
See application file for complete search history.

(56) References Cited

U.S. PATENT DOCUMENTS

| 10,221,198 B2 | 3/2019 | Severin |
| 2014/0274782 A1 | 9/2014 | Carlson |

OTHER PUBLICATIONS

Nwajiobi et al (Angew.Chem., 2021, 133, 7420-7428). (Year: 2021).*
Kimball et al (Angew.Chem.Int.Ed., 2002, 41, 3338-3351). (Year: 2002).*
Addy et al. A Chemoselective Rapid Azo-Coupling Reaction (CRACR) for Unclickable Bioconjugation, J. Am. Chem. Soc. 2017, 139, 11670-11673.
Blum et al. Using Azido Analogue of S-Adenosyl-L-methionine for Bioorthogonal Profiling of Protein Methylation (BPPM), Curr Protoc Chem Biol. 2013, 5: 45-66.
Chen et al. Genetic Incorporation of a 2-Naphthol Group into Proteins for Site-Specific Azo Coupling, Bioconjugate Chem. 2013, 24, 1645-1649.
Cornali et al. Cu-Click Compatible Triazabutadienes to Expand the Scope of Aryl Diazonium Ion Chemistry, Org. Lett. 2016, 18, 4948-4950.
Gavilyuk et al. Formylbenzene Diazonium Hexafluorophosphate Reagent for Tyrosine-Selective Modification of Proteins and the Introduction of a Bioorthogonal Aldehyde, Bioconjugate Chem. 2012, 23, 2321-2328.
Mahesh et al. Bioinspired Nitroalkylation for Selective Protein Modification and Peptide Stapling, Angew. Chem. Int. Ed. 2020, 59, 2793-2801.
Sengupta et al. Modifications of amino acids using arenediazonium salts, Org. Biomol. Chem., 2019, 17, 8308.
Sim et al. Secondary amine selective Petasis (SASP) bioconjugation, Chem. Sci., 2020, 11, 53.
Sonousi et al. Selective Protection of Secondary Amines as the N-Phenyltriazenes. Application to Aminoglycoside Antibiotics, Org. Lett. 2015, 17, 4006-4009.
Torres et al. Triazene as a Powerful Tool for Solid-Phase Derivatization of Phenylalanine Containing Peptides: Zygosporamide Analogues as a Proof of Concept, J. Org. Chem. 2014, 79, 11409-11415.
Vaughan et al. Triazenes: Synthesis and Chemical Properties, Triazenes, Edited by T. Giraldi et at. Plenum Press, New York, 1990 , p. 1-2.

\* cited by examiner

*Primary Examiner* — Sudhakar Katakam
(74) *Attorney, Agent, or Firm* — Emory Patent Group

(57) ABSTRACT

This disclosure relates to compositions and methods for selective labeling of N-alkyl lysine, N-alkyl adenosine, proline, N-alkyl cytosine, peptides, nucleic acids, or aliphatic or aromatic secondary amines. In certain embodiments, this disclosure relates to methods of forming triazene labeled compounds comprising contacting a compound containing a secondary amine group with a compound comprising an aromatic group with a diazonium para substituted with an electron rich group under conditions such that a triazene labeled compound is formed at the secondary amine group.

8 Claims, 8 Drawing Sheets

Specification includes a Sequence Listing.

COMPOSITIONS AND METHODS FOR SELECTIVE LABELING OF SECONDARY AMINES

CROSS-REFERENCE TO RELATED APPLICATIONS

This application claims the benefit of U.S. Provisional Application No. 63/246,517 filed Sep. 21, 2021. The entirety of this application is hereby incorporated by reference for all purposes.

STATEMENT REGARDING FEDERALLY SPONSORED RESEARCH OR DEVELOPMENT

This invention was made with government support under CHE-2103515 awarded by the National Science Foundation. The government has certain rights in the invention.

INCORPORATION-BY-REFERENCE OF MATERIAL SUBMITTED AS AN XML FILE VIA THE OFFICE ELECTRONIC FILING SYSTEM

The Sequence Listing associated with this application is provided in XML format and is hereby incorporated by reference into the specification. The name of the XML file containing the Sequence Listing is 21186US.xml. The XML file is 7 KB, was created on Sep. 20, 2022, and is being submitted electronically via the USPTO patent electronic filing system.

BACKGROUND

Lysine methylation in a protein is a posttranslational modification (PTM) involved in the regulation of various biological processes. Different levels of mono-, di-, and tri-methylation of lysine may result in different functions and localization within a cell. Controlling PTM of lysine, e.g., to monomethyl lysine (Kme), is reported in transcriptional activation and linked to numerous diseases and disorders such as heart disease, cancer, and diabetes. Methods to detect methylation of lysine are limited because the addition of a single methyl group leads to minor alteration in physicochemical properties of proteins such as steric bulk and hydrophobicity. Antibodies and other affinity reagents suffer from drawbacks. They are typically unable to completely detect all the methylation sites and unable to distinguish between different lysine methylation states (mono, di- or tri-). Another approach utilizes mass spectrometry (MS). However, MS analysis is limited as it does not directly confirm structural information and unable to detect low abundant lysine methylation PTMs. Thus, there is need to identify improved methods for detecting lysine methylation status.

Sengupta et al. report modifications of amino acids using arenediazonium salts. Org. Biomol. Chem., 2019, 17, 8308.

Sonousi et al. report selective protection of secondary amines as the N-phenyltriazenes. Org Lett, 2015, 17, 4006-4009.

Gavrilyuk et al. report formylbenzene diazonium hexafluorophosphate reagent for tyrosine-selective modification of proteins. Bioconjugate Chem, 2012, 23, 2321-2328.

Chen et al. report incorporation of a 2-naphthol group into proteins for site-specific azo coupling. Bioconjugate Chem, 2013, 24, 1645-1649.

Cornali et al. report Cu-click compatible triazabutadienes. Org Lett, 2016, 18, 4948-4950.

Addy et al. report chemoselective rapid azo-coupling reaction (CRACR) for unclickable bioconjugation. J Am Chem Soc, 2017, 139, 11670-11673.

Referenced cited herein are not an admission of prior art.

SUMMARY

This disclosure relates to compositions and methods for selective labeling of N-alkyl lysine, N-alkyl adenosine, proline, N-alkyl cytosine, peptides, nucleic acids, or aliphatic or aromatic secondary amines. In certain embodiments, this disclosure relates to methods of forming triazene labeled compounds comprising contacting a compound containing a secondary amine group with a compound comprising an aromatic group with a diazonium para substituted with an electron rich group under conditions such that a triazene labeled compound is formed at the secondary amine group.

In certain embodiments, the triazene labeled compound is an aliphatic secondary amine, proline, N-alkyl lysine, or peptide containing the same. In certain embodiments, the triazene labeled compound is an N-alkyl aromatic secondary amine such as N-alkyl adenosine, N-alkyl cytosine, or nucleic acids containing the same.

In certain embodiments, the triazene labeled compound is a secondary amine wherein nitrogen is substituted with two alkyl groups or wherein nitrogen is substituted with an alkyl group and an aromatic ring, i.e., aniline type aryl or heteroaryl. In certain embodiments, the compound comprising a secondary amine group is monomethyl lysine ($N^6$-methyl-lysine) or a peptide comprising monomethyl lysine. In certain embodiments, the compound comprising a secondary amine group is proline or a peptide comprising an N-terminal proline. In certain embodiments, the compound comprising a secondary amine group is $N^6$-alkyl or methyl adenosine and/or $N^4$-alkyl or methyl cytosine or DNA or RNA containing the same.

In certain embodiments, the compound comprising an aromatic group with a diazonium substituent para substituted with an electron rich group has the following formula,

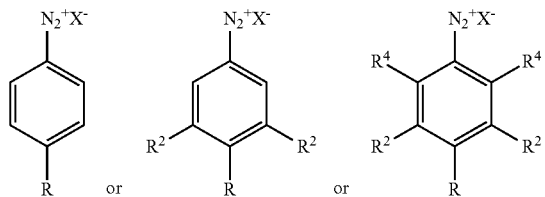

or derivatives thereof, wherein R is an electron rich group optionally substituted to a label or conjugated to a solid support through a linking group; and $X^-$ is a counter anion. In certain embodiments, R is a halogen, alkoxy, alkylthio, dialkylamino, acetamido, formyl, carboxyl, carbamoyl, or N-substituted carbamoyl group wherein R is optionally substituted with one or more substituents. In certain embodiments, $R^2$ or $R^4$ is individually and independently at each occurrence hydrogen or alkyl, wherein $R^2$ or $R^4$ are optionally substituted e.g., conjugated to a label or a solid support through a linking group, or $R^2$ or $R^4$ and the attached atoms together form an aromatic or non-aromatic ring optionally substituted e.g., conjugated to a label or a solid support through a linking group.

In certain embodiments, R is a linking group comprising an alkynyl group or R is —C=ONR$^1$, wherein R$^1$ is an alkynyl group. In certain embodiments, R$^2$ or R$^4$ is a linking group comprising an alkynyl group or R$^2$ or R$^4$ is —C=ONR$^1$, wherein R$^1$ is an alkynyl group.

In certain embodiments, the diazonium para substituted with an electron rich group is formed by the process of contacting para substituted aniline such as 4-amino-N-(alkynyl)benzamide with a nitrite salt, and a phosphate salt at pH of between 6.5 to 8.5.

In certain embodiments, the 4-amino-N-(alkynyl)benzamide is 4-amino-N-(prop-2-yn-1-yl)benzamide.

In certain embodiments, the conditions such that a triazene labeled compound is formed are in an aqueous solution with a pH of between 6.5 to 8.5.

In certain embodiments, this disclosure relates to methods of forming triazene labeled compounds comprising contacting a compound comprising a secondary amine group with a compound comprising an activated triazene which can be converted to diazonium in the presence of ultraviolet light providing an aromatic group with a diazonium para substituted with an electron rich group under conditions such that a triazene labeled compound is formed at the secondary amine group.

In certain embodiments, the compound comprising an aromatic group with an activated triazene has the following formula,

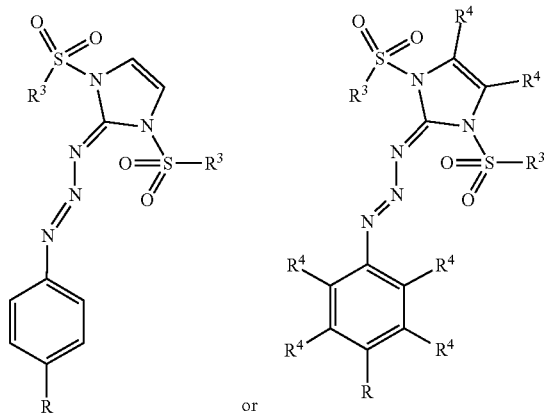

or derivatives or salts thereof, wherein R is an electron rich group or electron donating group optionally substituted or conjugated to a label or solid support through a linking group and R$^4$ is individually and independently at each occurrence hydrogen or alkyl, wherein R$^4$ is optionally substituted with one or more substituents, or two R$^4$ s and the attached atoms come together to form an aromatic or non-aromatic ring that is optionally substituted. In certain embodiments, R$^4$ is individually and independently at each occurrence hydrogen or alkyl, R$^4$ is optionally substituted e.g., conjugated to a label or a solid support through a linking group, or R$^4$ and the attached atoms together form an aromatic or non-aromatic ring optionally substituted e.g., conjugated to a label or a solid support through a linking group.

In certain embodiments, R is a halogen, alkoxy, alkylthio, dialkylamino, acetamido, formyl, carboxyl, carbamoyl, or N-substituted carbamoyl group wherein R is optionally substituted with one or more substituents. In certain embodiments, R is a linking group comprising an alkynyl group or R is —C=ONR$^1$, wherein R$^1$ is an alkynyl group.

In certain embodiments, this disclosure relates to methods of purifying a compound comprising a secondary amine in a sample comprising contacting the sample with 4-amino-N-(alkynyl)benzamide, a nitrite salt, and a phosphate salt at pH of about 7 providing a triazene labeled compound at the secondary amine having an alkynyl group in the sample; contacting the triazene labeled compound at the secondary amine having an alkynyl group in the sample with a solid support conjugated to a triazene group under conditions such that alkynyl group reacts with the triazene group on the solid support to form a triazole linkage providing a solid support conjugated to the triazene labeled compound at the secondary amine; washing the solid support to remove unreacted material from the sample providing a purified solid support conjugated to the triazene labeled compound at the secondary amine; and contacting the purified solid support conjugated to the triazene labeled compound at the secondary amine to acid conditions providing a composition with a purified compound comprising a secondary amine.

In certain embodiments, the compound comprising a secondary amine group is N$^6$-methyl-lysine or a peptide comprising N$^6$-methyl-lysine.

In certain embodiments, the compound comprising a secondary amine group is proline or a peptide comprising an N-terminal proline.

In certain embodiments, the compound comprising a secondary amine group is N$^6$-methyl adenosine or N$^4$-methyl cytosine or a DNA or RNA comprising N$^6$-methyl adenosine or N$^4$-methyl cytosine.

In certain embodiments, the 4-amino-N-(alkynyl)benzamide is 4-amino-N-(prop-2-yn-1-yl)benzamide.

In certain embodiments, the acid conditions include exposure to trifluoroacetic acid.

In certain embodiments, the methods further comprise determining the molecular weight of the peptide.

In certain embodiments, the methods further comprise separating the composition with a purified compound with a secondary amine into two or more compounds with a secondary amine. In certain embodiments, separating is by chromatography.

In certain embodiments, this disclosure relates to methods of purifying a compound with a secondary amine in a sample comprising, contacting the sample with a solid support conjugated to a compound comprising an aromatic group with a diazonium para substituted with an electron rich group such that the compounds with a secondary amine reacts with the diazonium providing the compound immobilized to the sold support; washing the solid support to remove unreacted material from the sample providing a purified compound immobilized to the sold support; and exposing the purified compound immobilized to the sold support to acid conditions releasing a purified compound with the secondary amine.

In certain embodiments, the compound comprising an aromatic group with a diazonium para substituted with an electron rich group is an activatable triazole, i.e., a triazole that transforms/decomposes to a diazonium when exposed to electromagnetic radiation.

In certain embodiments, the compound comprising a secondary amine group is N$^6$-methyl-lysine or a peptide comprising N$^6$-methyl-lysine.

In certain embodiments, the compound comprising a secondary amine group is proline or a peptide comprising an N-terminal proline.

In certain embodiments, the compound comprising a secondary amine group is N$^6$-methyl adenosine or N[4]-methyl cytosine or a DNA or RNA comprising N[6]-methyl adenosine or N[4]-methyl cytosine.

In certain embodiments, this disclosure relates to labeled compounds or solid supports, such as particles, coated with or conjugated to a compound having the following formula

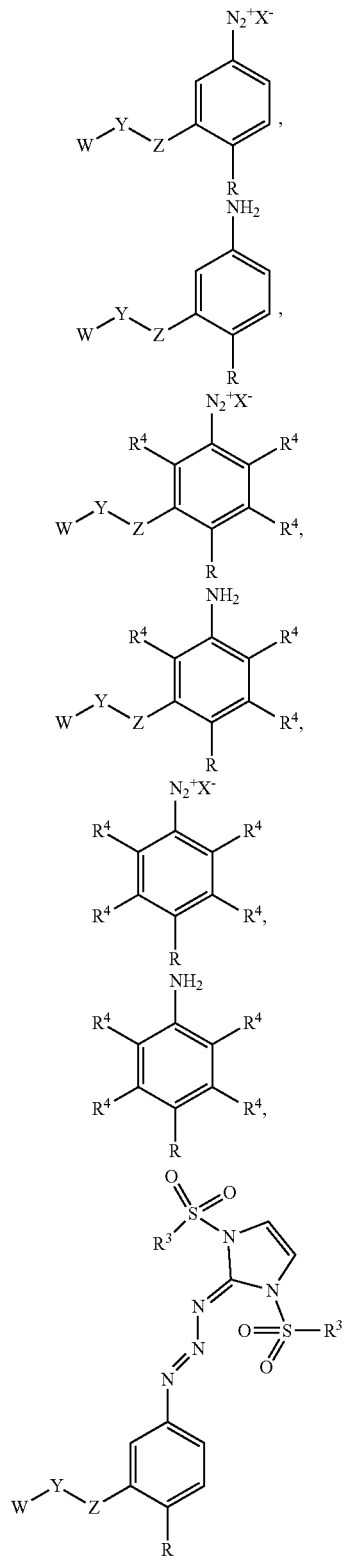

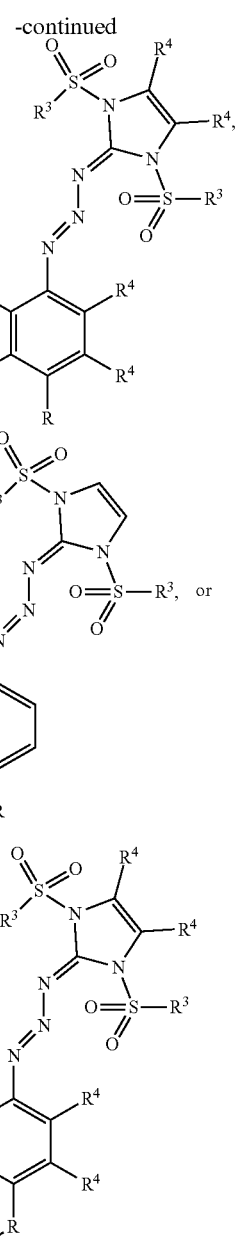

or derivative, or salt thereof wherein,
W is a solid support such as a particle or a label;
Y is O, NH, or S;
Z is a linking group;
R is an electron rich group or electron donating group;
$R^3$ is alkyl or phenyl, wherein $R^3$ is optionally substituted with one or more substituents,
$R^4$ is individually and independently at each occurrence hydrogen or alkyl, wherein $R^4$ is optionally substituted with one or more substituents, —Z—W, or —Z—Y—W, or two $R^4$s and the attached atoms come together to form an aromatic or non-aromatic ring that is optionally substituted with one or more substituents, —Z—W, or —Z—Y—W; and
$X^-$ is a counter anion.

In certain embodiments, R is a halogen, alkoxy, alkylthio, dialkylamino, acetamido, formyl, carboxyl, carbamoyl, or N-substituted carbamoyl group wherein R is optionally substituted with one or more substituents.

In certain embodiments, this disclosure relates to a labeled compound or solid support such as a particle conjugated with a compound having the following formula

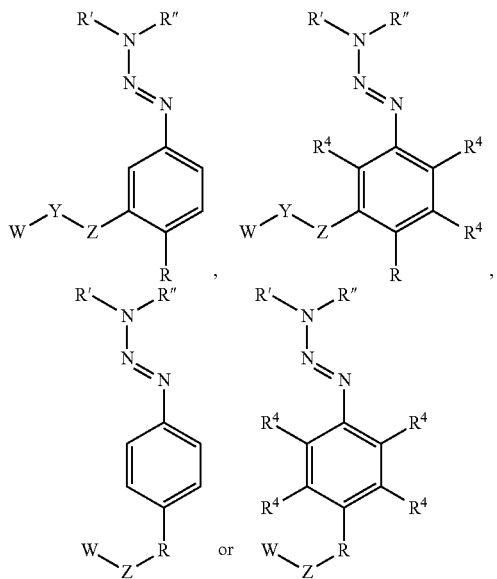

or derivative or salt thereof wherein,
W is a solid support such as a particle or a label;
Y is O, NH, or S;
Z is a linking group;
R is an electron rich group or electron donating group;
R' is an amino acid, nucleotide, peptide, nucleic acid, nucleobase polymer, adenosine, cytosine, or aromatic ring;
R" is alkyl such as methyl; or
R' and R" together with the attached nitrogen are a heterocyclyl such as a proline or N-terminal proline of a peptide, and
$R^4$ is individually and independently at each occurrence hydrogen or alkyl, wherein $R^4$ is optionally substituted with one or more substituents, —Z—W, or —Z—Y—W, or two $R^4$ s and the attached atoms come together to form an aromatic or non-aromatic ring that is optionally substituted with one or more substituents or —Z—W, or —Z—Y—W.

In certain embodiments, this disclosure relates to a compound or material comprising or coated with or conjugate to chemical arrangements disclosed herein.

In certain embodiments, a material, solid support, or particle further comprises or is coated with or conjugated to a hydrophilic polymer.

DETAILED DISCUSSION

Figure 1A:
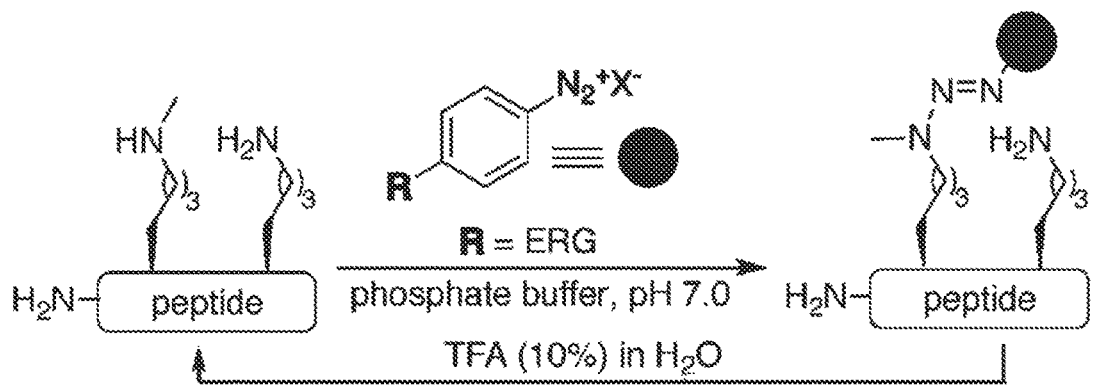
FIG. 1A illustrates a selective triazenation reaction with secondary amines. As a one-step approach, one can chemoselectively label secondary amines using electron-rich arene diazonium salts to give a stable triazene adduct under physiological conditions. Traceless cleavage of the triazene-coupling adduct can be accomplished under acidic conditions. Arene diazonium salts react with primary amines generating a reversible adduct making them unsuitable for tagging purposes at physiological pH.
Figure 1B:
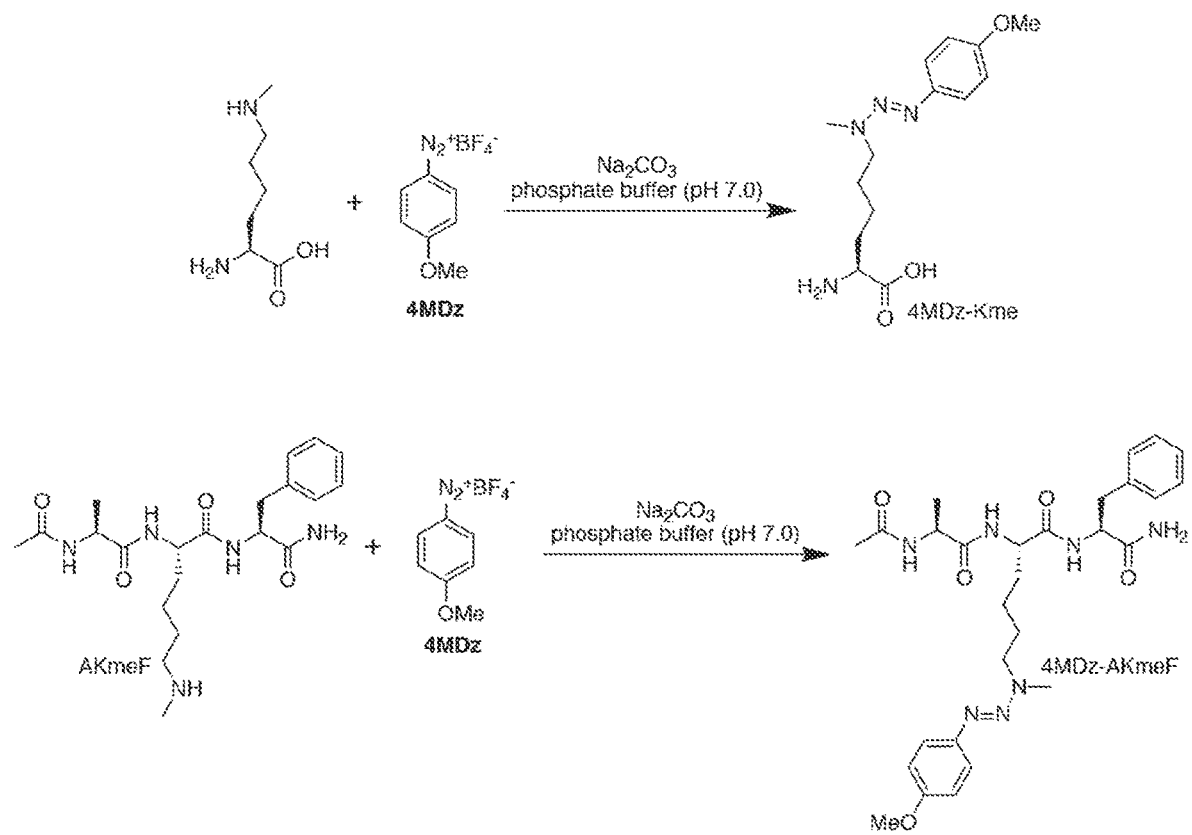
FIG. 1B illustrates at typical reaction. AKmeF (1 mg, 0.6 mM) in 4 mL of 100 mM phosphate buffer (pH 7.0) was added 4 MDz (1 equiv., 0.6 mM) followed by the addition of sodium carbonate $Na_2CO_3$ (1 equiv., 0.6 mM). The actual pH after addition of $Na_2CO_3$ is 8.3. The reaction was stirred at room temperature.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

An embodiment of this disclosure indicates that it is an example and not necessarily limited to such example. Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. In this specification and in the claims that follow reference will be made to a number of terms that shall be defined to have the following meanings unless a contrary intention is apparent.

As used in this disclosure and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") have the meaning ascribed to them in U.S. Patent law in that they are inclusive or open-ended and do not exclude additional, unrecited elements or method steps.

"Consisting essentially of" or "consists of" or the like, when applied to methods and compositions encompassed by the present disclosure refers to compositions like those disclosed herein that exclude certain prior art elements to provide an inventive feature of a claim, but which may contain additional composition components or method steps, etc., that do not materially affect the basic and novel characteristic(s) of the compositions or methods.

The terms "protein," "peptide," and "polypeptide" refer to compounds comprising amino acids joined via peptide bonds and are used interchangeably. As used herein, where "amino acid sequence" is recited herein to refer to an amino acid sequence of a protein molecule. An "amino acid sequence" can be deduced from the nucleic acid sequence encoding the protein. However, terms such as "peptide" or "protein" are not meant to limit be limited to natural amino acids. The term includes naturally and non-naturally derived material optionally having naturally or non-naturally occurring amino acids and modifications such as, substitutions, glycosylations, and addition of hydrophilic or lipophilic moieties. In certain embodiments, the protein/peptide/polypeptide comprises more than three, four, five, six, seven, eight, nine, or ten amino acids.

The term "nucleobase polymer" refers to a polymer comprising nitrogen containing aromatic or heterocyclic bases that bind to naturally occurring nucleic acids through hydrogen bonding otherwise known as base pairing. A typical nucleobase polymer is a nucleic acid, RNA, DNA, or chemically modified form thereof. A nucleobase polymer may contain DNA or RNA or a combination of DNA or RNA nucleotides or may be single or double stranded or both, e.g., they may contain overhangs, hairpins, bends, etc. Nucleobase polymers may contain naturally occurring or synthetically modified bases and backbones.

As used herein, the term "conjugated" refers to linking molecular entities through covalent bonds, or by other specific binding interactions, such as due to hydrogen bonding and other van der Walls forces. The force to break a covalent bond is high, e.g., about 1500 pN for a carbon-to-carbon bond. The force to break a combination of strong protein interactions is typically a magnitude less, e.g., biotin to streptavidin is about 150 pN. Thus, a skilled artisan would understand that conjugation must be strong enough to bind molecular entities in order to implement the intended results.

A "linking group" refers to any variety of molecular arrangements that can be used to bridge or conjugate molecular moieties together. An example formula may be $-R_n-$ wherein R is selected individually and independently at each occurrence as: $-CR_nR_n-$, $-CHR_n-$, $-CH-$, $-C-$, $-CH_2-$, $-C(OH)R_n-$, $-C(OH)(OH)-$, $-C(OH)H$, $-C(Hal)R_n-$, $-C(Hal)(Hal)-$, $-C(Hal)H-$, $-C(N_3) R_n-$, $-C(CN)R_n-$, $-C(CN)(CN)-$, $-C(CN)H-$, $-C(N_3)(N_3)-$, $-C(N_3)H-$, $-O-$, $-S-$, $-N-$, $-NH-$, $-NR_n-$, $-(C=O)-$, $-(C=NH)-$, $-(C=S)-$, $-(C=CH_2)-$, which may contain single, double, or triple bonds individually and independently between the R groups. If an R is branched with an $R_n$ it may be terminated with a group such as $-CH_3$, $-H$, $-CH=CH_2$, $-CCH$, $-OH$, $-SH$, $-NH_2$, $-N_3$, $-CN$, or -Hal, or two branched Rs may form an aromatic or non-aromatic cyclic structure. It is contemplated that in certain instances, the total Rs or "n" may be less than 100 or 50 or 25 or 10. Examples of linking groups include bridging alkyl groups, alkoxyalkyl, and aromatic groups.

The term "specific binding agent" refers to a molecule, such as a proteinaceous molecule, that binds a target molecule with a greater affinity than other random molecules or proteins. Examples of specific binding agents include antibodies that bind an epitope of an antigen or a receptor which binds a ligand. "Specifically binds" refers to the ability of a specific binding agent (such as an ligand, receptor, enzyme, antibody or binding region/fragment thereof) to recognize and bind a target molecule or polypeptide, such that its affinity (as determined by, e.g., affinity ELISA or other assays) is at least 10 times as great, but optionally 50 times as great, 100, 250 or 500 times as great, or even at least 1000 times as great as the affinity of the same for any other or other random molecule or polypeptide.

As used herein, the term "ligand" refers to any organic molecule, i.e., substantially comprised of carbon, hydrogen, and oxygen, that specifically binds to a "receptor." Receptors are organic molecules typically found on the surface of a cell. Through binding a ligand to a receptor, the cell has a signal of the extra cellular environment which may cause changes inside the cell. As a convention, a ligand is usually used to refer to the smaller of the binding partners from a size standpoint, and a receptor is usually used to refer to a molecule that spatially surrounds the ligand or portion thereof. However as used herein, the terms can be used interchangeably as they generally refer to molecules that are specific binding partners. For example, a glycan may be expressed on a cell surface glycoprotein and a lectin protein may bind the glycan. As the glycan is typically smaller and surrounded by the lectin protein during binding, it may be considered a ligand even though it is a receptor of the lectin binding signal on the cell surface. An antibody may be a receptor, and the epitope may be considered the ligand. In certain embodiments, a ligand is contemplated to be a compound that has a molecular weight of less than 500 or 1,000. In certain embodiments, a receptor is contemplated to be a protein-based compound that has a molecular weight of greater than 1,000, 2,000 or 5,000. In any of the embodiments disclosed herein the position of a ligand and a receptor may be switched.

A "label" refers to a detectable compound or composition that is conjugated directly or indirectly to another molecule, such as an antibody or a protein, to facilitate detection of that molecule. Specific, non-limiting examples of labels include fluorescent tags, enzymatic linkages, and radioactive isotopes. In one example, a peptide "label" refers to incorporation of a heterologous polypeptide in the peptide, wherein the heterologous sequence can be identified by a specific binding agent, antibody, or bind to a metal such as nickel/nitrilotriacetic acid, e.g., a poly-histidine sequence. Specific binding agents and metals can be conjugated to solid surfaces to facilitate purification methods. A label includes the incorporation of a radiolabeled amino acid or the covalent attachment of biotinyl moieties to a polypeptide that can be detected by marked avidin (for example, streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes or radionucleotides (such as $^{35}$S or $^{131}$I), fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels may be attached by spacer arms of various lengths to reduce potential steric hindrance.

In certain contexts, an "antibody" refers to a protein-based molecule that is naturally produced by animals in response to the presence of a protein or other molecule or that is not recognized by the animal's immune system to be a "self" molecule, i.e. recognized by the animal to be a foreign molecule and an antigen to the antibody. The immune system of the animal will create an antibody to specifically bind the antigen, and thereby targeting the antigen for elimination or degradation. It is well recognized by skilled artisans that the molecular structure of a natural antibody can be synthesized and altered by laboratory techniques. Recombinant engineering can be used to generate fully synthetic antibodies or fragments thereof providing control over variations of the amino acid sequences of the antibody. Thus, as used herein the term "antibody" is intended to include natural antibodies, monoclonal antibody, or non-naturally produced synthetic antibodies, and binding fragments, such as single chain binding fragments. These antibodies may have chemical modifications. The term "monoclonal antibodies" refers to a collection of antibodies encoded by the same nucleic acid molecule that are optionally produced by a single hybridoma (or clone thereof) or other cell line, or by a transgenic mammal such that each monoclonal antibody will typically recognize the same antigen. The term "monoclonal" is not limited to any particular method for making the antibody, nor is the term limited to antibodies produced in a particular species, e.g., mouse, rat, etc.

Hydrophilic polymers contain polar or charged functional groups, rendering them soluble in water. Examples include polyethylene glycol, polylactides, polyglycolide, poly(ε-caprolactone), poly(2-methoxyethyl acrylate), poly(tetrahydrofurfuryl acrylate), poly(2-methacryloyloxyethyl phosphorylcholine), poly(p-dioxanone), poly(serine methacrylate), poly[oligo (ethylene glycol) vinyl ether], poly{[2-(methacryloyloxy)ethyl]}, copolymers of ethylene glycol and propylene glycol, poly(oxyethylated polyol), poly(olefmic alcohol), poly(vinylpyrrolidone), poly(hydroxyalkylmethacrylamide), poly(hydroxyalkylmethacrylate), poly(saccharides), poly(alpha-hydroxy acid), and poly (vinyl alcohol). "PEG," "polyethylene glycol" and "poly (ethylene glycol)" refers to water-soluble poly(ethylene oxide). Typically, PEGs comprise the following structure "—(OCH$_2$CH$_2$)n-" where (n) is 2 to 4000.

As used herein, the term "derivative" refers to a structurally similar compound that retains sufficient functional attributes of the identified analogue. The derivative may be structurally similar because it is lacking one or more atoms, substituted, a salt, in different hydration/oxidation states, or because one or more atoms within the molecule are switched, such as, but not limited to, replacing an oxygen atom with a sulfur atom, replacing an amino group with a hydroxyl group, replacing a nitrogen with a protonated carbon (CH) in an aromatic ring, replacing a bridging amino group (—NH—) with an oxy group (—O—), or vice versa. The derivative may be a prodrug. A derivative may be a polypeptide variant. Derivatives may be prepared by any variety of synthetic methods or appropriate adaptations presented in synthetic or organic chemistry textbooks, such as those provide in March's Advanced Organic Chemistry: Reactions, Mechanisms, and Structure, Wiley, 6th Edition (2007) Michael B. Smith or Domino Reactions in Organic Synthesis, Wiley (2006) Lutz F. Tietze hereby incorporated by reference.

The term "substituted" refers to a molecule wherein at least one hydrogen atom is replaced with a substituent. When substituted, one or more of the groups are "substituents." The molecule may be multiply substituted. In the case of an oxo substituent ("=O"), two hydrogen atoms are replaced. Example substituents within this context may include halogen, hydroxy, alkyl, alkoxy, nitro, cyano, carbocyclyl, carbocycloalkyl, heterocarbocyclyl, heterocarbocycloalkyl, aryl, arylalkyl, heteroarylalkyl, —NR$_a$R$_b$, —NR$_a$C(=O)R$_b$, —NR$_a$C(=O)NR$_a$NR$_b$, —NR$_a$C(=O)OR$_b$, —NR$_a$SO$_2$R$_b$, —C(=O)R$_a$, —C(=O)OR$_a$, —C(=O)NR$_a$R$_b$, —OC(=O)NR$_a$R$_b$, —OR$_a$, —SR$_a$, —SOR$_a$, —S(=O)$_2$R$_a$, —OS(=O)$_2$R$_a$ and —S(=O)$_2$OR$_a$. R$_a$ and R$_b$ in this context may be the same or different and independently hydrogen, halogen hydroxyl, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, and heteroarylalkyl.

As used herein, "alkyl" means a noncyclic straight chain or branched, unsaturated or saturated hydrocarbon such as those containing from 1 to 10 carbon atoms. Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

"Alkylthio" refers to an alkyl group as defined above with the indicated number of carbon atoms attached through a sulfur bridge. An example of an alkylthio is methylthio, (i.e., —S—CH$_3$).

"Alkoxy" refers to an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, i-propoxy, n-butoxy, s-butoxy, t-butoxy.

"Alkylamino" refers an alkyl group as defined above with the indicated number of carbon atoms attached through an amino bridge. An example of an alkylamino is methylamino, (i.e., —NH—CH$_3$).

"Alkanoyl" refers to an alkyl as defined above with the indicated number of carbon atoms attached through a carbonyl bride (i.e., —(C=O)alkyl).

"Alkylthio" refers to an alkyl group as defined above with the indicated number of carbon atoms attached through a sulfur bridge. An example of an alkylthio is methylthio, (i.e., —S—CH$_3$).

"Alkoxy" refers to an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, i-propoxy, n-butoxy, s-butoxy, t-butoxy.

"Alkylamino" refers an alkyl group as defined above with the indicated number of carbon atoms attached through an amino bridge. An example of an alkylamino is methylamino, (i.e., —NH—CH$_3$).

"Alkanoyl" refers to an alkyl as defined above with the indicated number of carbon atoms attached through a carbonyl bride (i.e., —(C=O)alkyl).

"Aryl" means an aromatic carbocyclic monocyclic or polycyclic ring such as phenyl or naphthyl. Polycyclic ring systems may, but are not required to, contain one or more non-aromatic rings, as long as one of the rings is aromatic.

Non-aromatic mono or polycyclic alkyls are referred to herein as "carbocycles" or "carbocyclyl" groups. Representative saturated carbocycles include cyclopropyl, cyclobutyl, cyclopentyl, cyclohexyl, and the like; while unsaturated carbocycles include cyclopentenyl and cyclohexenyl, and the like As used herein, "heterocycle" or "heterocyclyl" refers to mono- and polycyclic ring systems having 1 to 4 heteroatoms selected from nitrogen, oxygen and sulfur, and containing at least 1 carbon atom. The mono- and polycyclic ring systems may be aromatic, non-aromatic or mixtures of aromatic and non-aromatic rings. Heterocycle includes heterocarbocycles, heteroaryls, and the like.

As used herein, "heteroaryl" or "heteroaromatic" refers an aromatic heterocarbocycle having 1 to 4 heteroatoms selected from nitrogen, oxygen and sulfur, and containing at least 1 carbon atom, including both mono- and polycyclic ring systems. Polycyclic ring systems may, but are not required to, contain one or more non-aromatic rings, as long as one of the rings is aromatic. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl. It is contemplated that the use of the term "heteroaryl" includes N-alkylated derivatives such as a 1-methylimidazol-5-yl substituent.

Methods and Compositions for Detecting Secondary Amines Such as Monomethyl Lysine, Proline, and Proteins Comprising the Same and Secondary Amines N$^6$-Alkyl or Methyl Adenosine and N$^4$-Alkyl or Methyl Cytosine or a DNA or RNA Comprising the Same This disclosure relates to methods of forming triazene labeled compounds comprising contacting a compound comprising a secondary amine group with a compound comprising an aromatic group with a diazonium para substituted with an electron rich group under conditions such that a triazene labeled compound is formed with the secondary amine group.

In certain embodiments, the compound comprising a secondary amine group is monomethyl lysine (N$^6$-methyllysine) or a protein comprising monomethyl lysine. In certain embodiments, the compound comprising a secondary amine group is proline or a protein comprising an N-terminal proline. In certain embodiments, the compound comprising a secondary amine group is $N^6$-methyl adenosine or $N^4$-methyl cytosine or a DNA or RNA comprising $N^6$-methyl adenosine or $N^4$-methyl cytosine.

In certain embodiments, the compound comprising an aromatic group with a diazonium substituent para substituted with an electron rich group has the following formula,

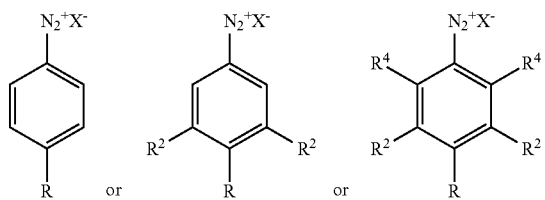

or derivatives thereof, wherein R is an electron rich group optionally substituted or conjugated to a label or a solid support through a linking group; and $X^-$ is a counter anion. In certain embodiments, R is a halogen, alkoxy, alkylthio, dialkylamino, acetamido, formyl, carboxyl, carbamoyl, or N-substituted carbamoyl group wherein R is optionally substituted with one or more substituents. In certain embodiments, $R^2$ is individually and independently at each occurrence hydrogen or alkyl, wherein $R^2$ is optionally substituted e.g., conjugated to a label or a solid support through a linking group. In certain embodiments, $R^2$ or $R^4$ is individually and independently at each occurrence hydrogen or alkyl, wherein $R^2$ or $R^4$ are optionally substituted e.g., conjugated to a label or a solid support through a linking group. In certain embodiments, $R^2$ and $R^4$ and the attached atoms come together to form an aromatic or non-aromatic ring optionally substituted e.g., conjugated to a label or a solid support through a linking group.

In certain embodiments, R is a linking group comprising an alkynyl group or R is —C—ONR$^1$, wherein $R^1$ is an alkynyl group. In certain embodiments, $R^2$ is a linking group comprising an alkynyl group or R is —C=ONR$^1$, wherein $R^1$ is an alkynyl group.

In certain embodiments, the diazonium para substituted with an electron rich group is formed by the process of contacting para substituted aniline, such as 4-amino-N-(alkynyl)benzamide, with a nitrite salt, and a phosphate salt at pH of between 6.5 to 8.5.

In certain embodiments, the 4-amino-N-(alkynyl)benzamide is 4-amino-N-(prop-2-yn-1-yl)benzamide.

In certain embodiments, the conditions such that a triazene labeled compound is formed are in an aqueous solution with a pH of between 6.5 to 8.5.

In certain embodiments, the diazonium para substituted with an electron rich group is formed by the process of exposing a compound comprising an aromatic group with an activatable triazene substituent para substituted with an electron rich group to ultraviolet light.

In certain embodiments, the compound comprising an aromatic group with an activated triazene has the following formula,

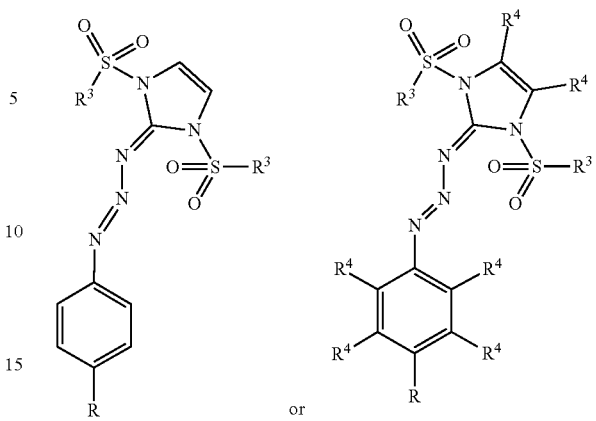

or derivatives or salts thereof, wherein R is an electron rich group or electron donating group optionally substituted or conjugated to a label or solid support through a linking group and $R^4$ is individually and independently at each occurrence hydrogen or alkyl, wherein $R^4$ is optionally substituted with one or more substituents, or two $R^4$ s and the attached atoms come together to form an aromatic or non-aromatic ring that is optionally substituted. In certain embodiments, R is a halogen, alkoxy, alkylthio, dialkylamino, acetamido, formyl, carboxyl, carbamoyl, or N-substituted carbamoyl group wherein R is optionally substituted with one or more substituents. In certain embodiments, R is a linking group comprising an alkynyl group or R is —C—ONR$^1$, wherein $R^1$ is an alkynyl group.

In certain embodiments, this disclosure relates to methods of purifying a compound comprising a secondary amine in a sample comprising contacting the sample with 4-amino-N-(alkynyl)benzamide, a nitrite salt, and a phosphate salt at pH of about 7 providing a triazene labeled compound at the secondary amine having an alkynyl group in the sample; contacting the triazene labeled compound at the secondary amine having an alkynyl group in the sample with a solid support conjugated to a triazene group under conditions such that alkynyl group reacts with the triazene group on the solid support to form a triazole linkage providing a solid support conjugated to the triazene labeled secondary amine; purifying or washing the solid support to remove unreacted material from the sample providing a purified solid support conjugated to the triazene labeled secondary amine; and contacting the purified solid support conjugated to the triazene labeled secondary amine to acid conditions providing a composition with a purified secondary amine.

In certain embodiments, the methods further comprise separating the composition with a purified compound with a secondary amine into two or more compounds comprising the secondary amine. In certain embodiments, separating is by chromatography.

In certain embodiments, this disclosure contemplates that the solid support is a magnetic material, e.g., magnetic bead, and purifying is capturing the magnetic bead with a magnetic field thereby separating the magnetic bead and contents thereof from a solution or mixture.

In certain embodiments, the 4-amino-N-(alkynyl)benzamide is 4-amino-N-(prop-2-yn-1-yl)benzamide.

In certain embodiments, the acid conditions include exposure to trifluoroacetic acid.

In certain embodiments, this disclosure relates to methods of purifying a protein comprising monomethyl lysine ($N^6$- methyl-lysine) in a sample comprising contacting the sample with 4-amino-N-(alkynyl)benzamide, a nitrite salt, and a phosphate salt at pH of about 7 providing a triazene labeled protein at the $N^6$-methyl-lysine having an alkynyl group in the sample; contacting the triazene labeled protein at the $N^6$-methyl-lysine having an alkynyl group in the sample with a solid support conjugated to a triazene group under conditions such that alkynyl group reacts with the triazene group on the solid support to form a triazole linkage providing a solid support conjugated to the triazene labeled protein at the $N^6$-methyl-lysine; purifying or washing the solid support to remove unreacted material from the sample providing a purified solid support conjugated to the triazene labeled protein at the $N^6$-methyl-lysine; and contacting the purified solid support conjugated to the triazene labeled protein at the $N^6$-methyl-lysine to acid conditions providing a composition with a purified protein comprising $N^6$-methyl-lysine.

In certain embodiments, this disclosure contemplates that the solid support is a magnetic material, e.g., magnetic bead, and purifying is capturing the magnetic bead with a magnetic field thereby separating the magnetic bead and contents thereof from a solution or mixture.

In certain embodiments, the 4-amino-N-(alkynyl)benzamide is 4-amino-N-(prop-2-yn-1-yl)benzamide.

In certain embodiments, the acid conditions include exposure to trifluoroacetic acid.

In certain embodiments, the methods further comprise determining the molecular weight of the protein.

In certain embodiments, the methods further comprise separating the composition with a purified protein comprising $N^6$-methyl-lysine into two or more proteins comprising $N^6$-methyl-lysine. In certain embodiments, separating is by chromatography.

In certain embodiments, this disclosure relates to methods of purifying a nucleic acid comprising N-methylated or N-alkylated adenosine or N-methylated or N-alkylated cytosine in a sample comprising: contacting the sample with 4-amino-N-(alkynyl)benzamide, a nitrite salt, and a phosphate salt at pH of about 7 providing a triazene labeled nucleic acid at the N-methylated or N-alkylated adenosine or N-methylated or N-alkylated cytosine having an alkynyl group in the sample; contacting the triazene labeled nucleic acid at the N-methylated or N-alkylated adenosine or N-methylated or N-alkylated cytosine having an alkynyl group in the sample with a solid support conjugated to a triazene group under conditions such that alkynyl group reacts with the triazene group on the solid support providing a solid support conjugated to the triazene labeled nucleic acid at the N-methylated or N-alkylated adenosine or N-methylated or N-alkylated cytosine; washing the solid support to remove unreacted material from the sample providing a purified solid support conjugated to the triazene labeled nucleic acid at the N-methylated or N-alkylated adenosine or N-methylated or N-alkylated cytosine; and contacting the purified solid support conjugated to the triazene labeled nucleic acid at the N-methylated or N-alkylated adenosine or N-methylated or N-alkylated cytosine to acid conditions providing a composition with a purified nucleic acid at the N-methylated or N-alkylated adenosine or N-methylated or N-alkylated cytosine.

In certain embodiments, the methods further comprise separating the composition with a purified protein comprising N-methylated or N-alkylated adenosine or N-methylated or N-alkylated cytosine into two or more proteins comprising N-methylated or N-alkylated adenosine or N-methylated or N-alkylated cytosine. In certain embodiments, separating is by chromatography.

In certain embodiments, this disclosure relates to methods of purifying a protein comprising secondary amine in a sample comprising, contacting the sample with a solid support conjugated to a compound comprising an aromatic group with a diazonium para substituted with an electron rich group such that secondary amine with the diazonium providing the compound immobilized to the sold support; washing the solid support to remove unreacted material from the sample providing a purified compound immobilized to the sold support; and exposing the purified compound immobilized to the sold support to acid conditions releasing a purified secondary amine.

In certain embodiments, this disclosure relates to methods of purifying a protein comprising monomethyl lysine ($N^6$-methyl-lysine) or proline in a sample comprising, contacting the sample with a solid support conjugated to a compound comprising an aromatic group with a diazonium para substituted with an electron rich group such that the $N^6$-methyl-lysine or proline reacts with the diazonium providing the protein immobilized to the sold support; washing the solid support to remove unreacted material from the sample providing a purified a purified protein immobilized to the sold support; and exposing the purified protein immobilized to the sold support to acid conditions releasing a purified protein comprising $N^6$-methyl-lysine.

In certain embodiments, this disclosure relates to methods of purifying a nucleic acid comprising N-methylated or N-alkylated adenosine or N-methylated or N-alkylated cytosine in a sample comprising, contacting the sample with a solid support conjugated to a compound comprising an aromatic group with a diazonium para substituted with an electron rich group such that N-methylated or N-alkylated adenosine or N-methylated or N-alkylated cytosine reacts with the diazonium providing the nucleic acid immobilized to the sold support; washing the solid support to remove unreacted material from the sample providing a purified a purified nucleic acid immobilized to the sold support; and exposing the purified nucleic acid immobilized to the sold support to acid conditions releasing a purified nucleic acid comprising N-methylated or N-alkylated adenosine or N-methylated or N-alkylated cytosine.

In certain embodiments, this disclosure relates to labeled compounds or solid supports, such as particles, coated with or conjugated to a compound having the following formula

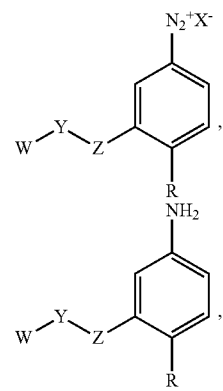

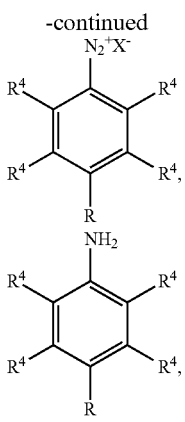

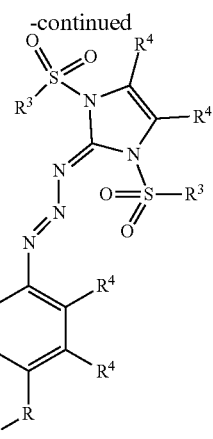

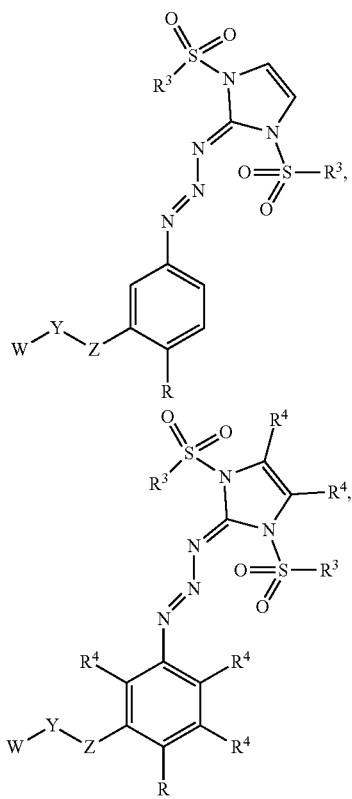

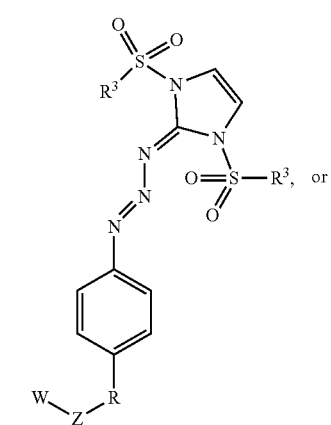

or derivative, or salt thereof wherein,
W is a solid support such as a particle or a label;
Y is O, NH, or S;
Z is a linking group;
R is an electron rich group or electron donating group;
$R^3$ is alkyl or phenyl optionally substituted with one or more substituents;
$R^4$ is individually and independently at each occurrence hydrogen or alkyl, wherein $R^4$ is optionally substituted with one or more substituents, —Z—W, or —Z—Y—W, or two $R^4$s and the attached atoms come together to form an aromatic or non-aromatic ring that is optionally substituted with one or more substituents or —Z—W, or —Z—Y—W; and
$X^-$ is a counter anion.

In certain embodiments, R is a halogen, alkoxy, alkylthio, dialkylamino, acetamido, formyl, carboxyl, carbamoyl, or N-substituted carbamoyl group wherein R is optionally substituted with one or more substituents.

In certain embodiments, this disclosure relates to a labeled compound or solid support such as a particle coated or conjugated to with a compound having the following formula

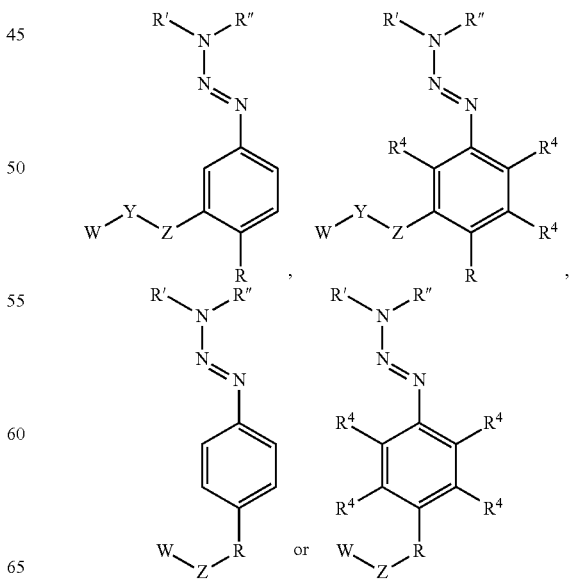

or derivative or salt thereof wherein,
W is a solid support such as a particle or a label;
Y is O, NH, or S;
Z is a linking group;
R is an electron rich group or electron donating group;
R' is an amino acid, nucleotide, protein, nucleic acid, nucleobase polymer, adenosine, cytosine, or aromatic ring;
R" is alkyl such as methyl; or
R' and R" together with the attached nitrogen are a heterocyclyl such as a proline or N-terminal proline of a protein, and
$R^4$ is individually and independently at each occurrence hydrogen or alkyl, wherein $R^4$ is optionally substituted with one or more substituents, —Z—W, or —Z—Y—W, or two $R^4$s and the attached atoms come together to form an aromatic or non-aromatic ring that is optionally substituted with one or more substituents or —Z—W, or —Z—Y—W.

In certain embodiments, this disclosure relates to a compound having the following formula

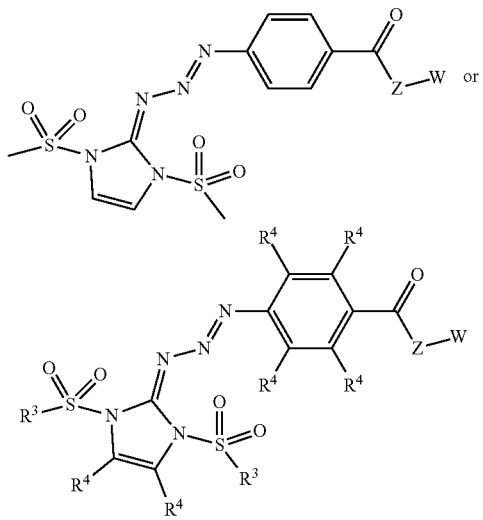

or salt thereof wherein,
W is a solid surface or particle or a label;
Z is a linking group;
$R^3$ is alkyl or phenyl optionally substituted with one or more substituents; and
$R^4$ is individually and independently at each occurrence hydrogen or alkyl, wherein $R^4$ is optionally substituted with one or more substituents, or —Z—W, or two $R^4$s and the attached atoms come together to form an aromatic or non-aromatic ring that is optionally substituted with one or more substituents or —Z—W.

In certain embodiments, this disclosure relates to the compound (E)-4-((1,3-bis(methylsulfonyl)-1,3-dihydro-2H-imidazol-2-ylidene)triaz-1-en-1-yl)benzoic acid,

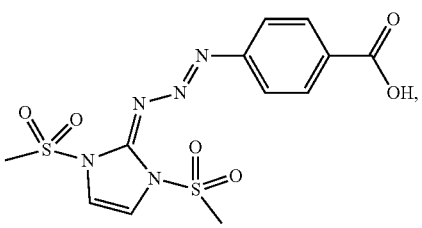 [SMILES: CS(=O)(=O)n1ccn(S(C)(=O)=O)c1=N/N=N/c1ccc(C(=O)O)cc1]

or derivative or salt thereof.

In certain embodiments, this disclosure relates to the compound ((E)-4-((1,3-bis(methylsulfonyl)-1,3-dihydro-2H-imidazol-2-ylidene)triaz-1-en-1-yl)-N-(2-(5-(2-oxohexahydro-1H-thieno[3,4-d]imidazol-4-yl)pentanamido)ethyl)benzamide

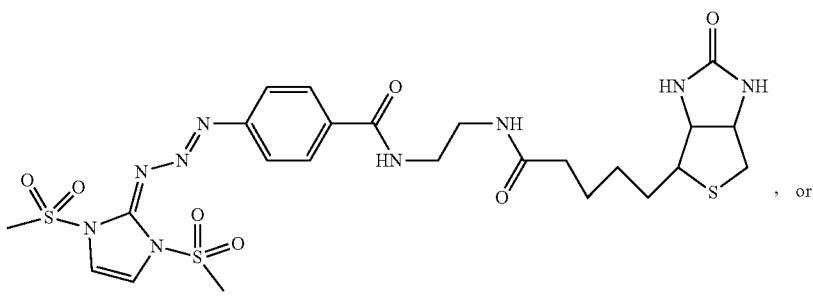 [SMILES: CS(=O)(=O)n1ccn(S(C)(=O)=O)c1=N/N=N/c1ccc(C(=O)NCCNC(=O)CCCCC2SCC3NC(=O)NC32)cc1 ; "," ; "or"]

derivative or salt thereof.

In certain embodiments, this disclosure relates to methods of making diazonium compounds by contacting a compound or a compound having a formula as provided above, e.g., with a 4-((1,3-bis(methylsulfonyl)-1,3-dihydro-2H-imidazol-2-ylidene)triaz-1-en-yl)benzamide or 4-((1,3-bis(methylsulfonyl)-1,3-dihydro-2H-imidazol-2-ylidene)triaz-1-en-yl)benzaldehyde, 4-((1,3-bis(methylsulfonyl)-1,3-dihydro-2H-imidazol-2-ylidene)triaz-1-en-yl)benzoic acid or derivative thereof, with ultraviolet light under conditions providing a diazonium salt.

In certain embodiments, this disclosure relates to methods of contacting a secondary amine or compound or protein containing a secondary amine or monomethyl lysine wherein the secondary amine or compound or protein containing a secondary amine or monomethyl lysine is in a sample such as a biological sample, (e.g., cell, tissue, etc.) or environmental sample. Biological samples may be obtained from animals (including humans) and encompass fluids, blood, solids, tissues, and gases. Environmental samples include environmental material such as surface matter, soil, water, and industrial samples.

Selective Triazenation Reaction with Secondary Amines

One can introducing various functionalities in arene diazonium salts. Arene diazonium ions are capable of forming triazenes with primary amines; however, this has never been pursued as a bioconjugation method because of its reversible nature at physiological pH. The azo-coupling of arene diazonium ion with tyrosine is reported for bioconjugation. This process requires an electrophilic arene diazonium ion with electron withdrawing groups for carrying out the reaction under physiological conditions. (pH 7.4). The less electrophilic counterparts are only able to react with Tyr at a significantly elevated pH (9.0). Moreover, it has been reported that reaction with Cys is low yielding under physiological conditions (pH 7.5), especially with electron rich diazonium ions. Experiments were performed to determine whether less electrophilic arene diazonium salts with electron donating substituents would facilitate chemoselective reaction for secondary amines (FIG. 1A).

Figure 2:
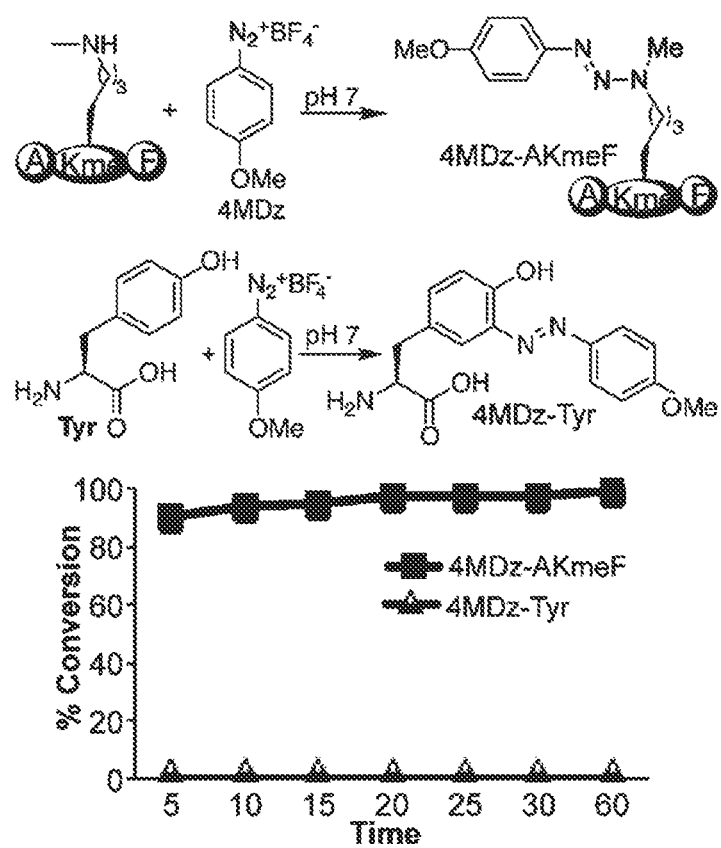
FIG. 2 shows a reaction with aryl diazonium ion with electron releasing group such as 4 MDz at pH 6-8.5 reacts selectively with secondary amine (monomethyl lysine) without the modification of tyrosine residues.

To evaluate the reactivity of secondary amines toward less electrophilic arene diazonium ions, an experiment was performed by reacting 4-methoxybenzenediazonium ion (4 MDz) and the amino acid, monomethyl lysine. The reaction between the monomethyl lysine (0.6 mm) and 4 MDz (0.6 mm) proceeds most efficiently in the presence of $Na_2CO_3$ (0.6 mm) in phosphate buffer (100 mm, pH 7) at room temperature, resulting in the formation of a stable triazene-coupling product with 99% conversion in 30 min. The triazene reaction was also run between 4 MDz (0.6 mm) with a monomethyl lysine protein, AKmeF (0.6 mm), after regular intervals of time. This reaction was compared to the corresponding reaction with tyrosine (0.6 mm) (phosphate buffer (100 mm), pH 7, FIG. 1A and FIG. 2). The formation of the chromophoric triazene coupling product was detected using spectrophotometry (increased absorption at 330-390 nm) and HPLC. The results showed 93% conversion to the triazene-coupling adduct in just 5 min as analyzed by HPLC (FIG. 2). The azo-coupling product was not observed with tyrosine even after 24 h. Similar reactivity and high selectivity towards monomethyl lysine was observed with another diazonium ion, 4-carboxybenzenediazonium (4CDz), upon reaction with the peptide GAKmeF (SEQ ID NO: 3) under optimized conditions (FIG. 2). To characterize the triazene-coupling products with 4 MDz, reactions with proline methyl ester, 2-(methylamino) ethanol and a peptide (NHMe)Ala-Phe-OMe containing secondary amines were carried out on a large scale under the reaction conditions. The resulting products were isolated and triazenation of secondary amines were confirmed by NMR ($^1$H and $^{13}$C). In contrast, no product was observed with alanine.

Secondary Amine Selective Triazenation Reactions with No-Alkyl or Methyl Adenosine and $N^4$-Alkyl or Methyl Cytosine or a DNA or RNA Comprising an $N^6$-Alkyl or Methyl Adenosine and $N^4$-Alkyl or Methyl Cytosine.

To evaluate the reactivity of aromatic secondary amines such as $N^6$-alkyl or methyl adenosine and $N^4$-alkyl or methyl cytosine toward less electrophilic arene diazonium ions, an experiment was performed by reacting 4-methoxybenzenediazonium ion (4 MDz) and the $N^6$-methyl adenosine and $N^4$-methyl cytosine. The reaction between the $N^6$-methyl adenosine (0.6 mm) and 4 MDz (0.6 mm) proceeds most efficiently in the presence of $Na_2CO_3$ (0.6 mm) in phosphate buffer (100 mm, pH 7) at room temperature, resulting in the formation of a stable triazene-coupling product with 89% conversion in 5 h. The triazene reaction was also run between 4 MDz (0.6 mm) with a $N^4$-methyl cytosine (0.6 mm). The formation of the chromophoric triazene coupling product was detected using spectrophotometry (increased absorption at 330-390 nm) and HPLC. The results showed 85% conversion to the triazene-coupling adduct in 5 h as analyzed by HPLC. The triazene-coupling product was not observed with adenosine and cytosine even after 24 h. Similar reactivity and high selectivity towards aromatic secondary amines was observed with another diazonium ion, 4-carboxybenzenediazonium (4CDz), upon reaction with $N^6$-methyl adenosine under optimized conditions.

Chemoselectivity of Selective Triazenation Reactions

Figure 3A:
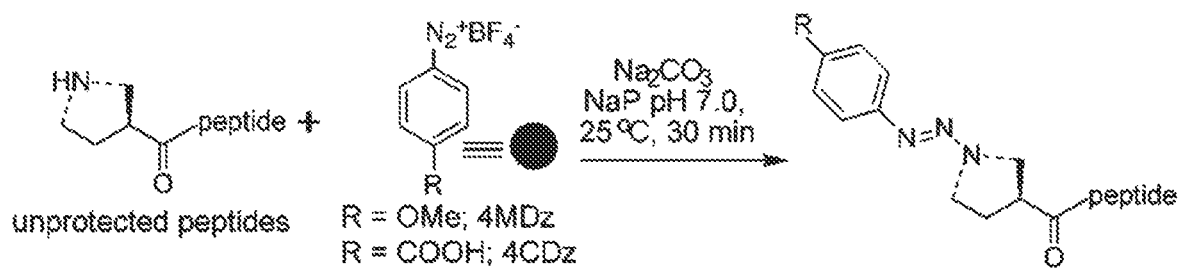
FIG. 3A shows data indicating secondary amine triazene formation using 4 MDz has high chemoselectivity for proline as quantified by LC/MS among a panel of reactive amino acids.
Figure 3A:
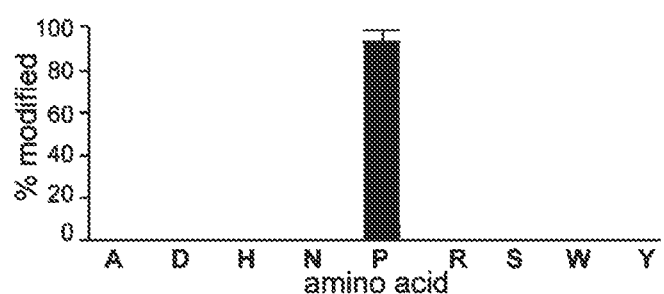
Figure 3B:
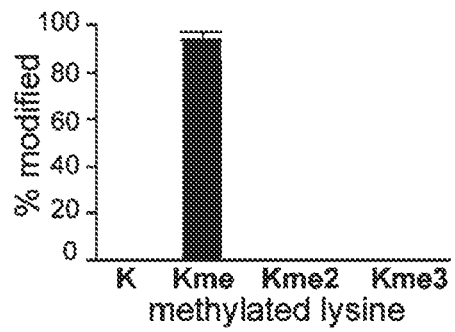
FIG. 3B shows data indicating secondary amine triazene formation using 4 MDz has high chemoselectivity for monomethyl lysine (Kme) among a panel of other methylated states of lysine as quantified by LC/MS.

To evaluate the chemoselective, 4-methoxybenzenediazonium (4 MDz) reactions were carried out with various reactive amino acids such as Ala, Asp, His, Asn, Pro, Arg, Ser, Trp, and Tyr under optimized reaction conditions. The reactions were monitored for 30 min, 2 h, and 24 h by LCMS. The data indicated the formation of triazene-coupling product with proline only (FIG. 3A). Further, reaction of 4 MDz with unmethylated lysine and various methylation states of lysine (Kme, Kme2, and Kme3) confirmed high chemoselectivity for the monomethyl lysine Kme (FIG. 3B). 4 MDz and 4-carboxybenzenediazonium (4CDz) were reacted with a variety of peptides of different sizes and amino acid composition containing monomethylated lysine at different positions. Peptides bearing aromatic and aliphatic amino acids next to the monomethyl lysine were fully tolerated in this protocol yielding the corresponding triazene-coupling products with excellent conversions. The reactions with a peptide GEPGIAGFKmeGEQGPK (collagen fragment, SEQ ID NO: 1) bearing reactive amino acids, such as Glu, Gln, and Lys, did not interrupt or influence the triazenation process, and afforded a desired triazene-coupling product with Kme in good conversion (85%). Interestingly, the peptide GKmeAKmeF (SEQ ID NO: 2) with two monomethyl lysines at the alternate position showed the double modification due to the formation of triazene-coupled product with both monomethyl lysines (89%). Together, these results confirmed the high chemoselectivity and pan specificity toward secondary amines. To test the high selectivity in a complex environment, a mixture of peptides PAF, AKmeF, GAKmeF (SEQ ID NO: 3), and GKmeAKmeF (SEQ ID NO: 2) was treated with 4 MDz and resulting solution was analyzed by LC-MS. Complete labeling of all the peptides was observed. These experiments indicate high pan-specificity of the reaction in a complex mixture under mild physiological conditions.

Figure 4A:
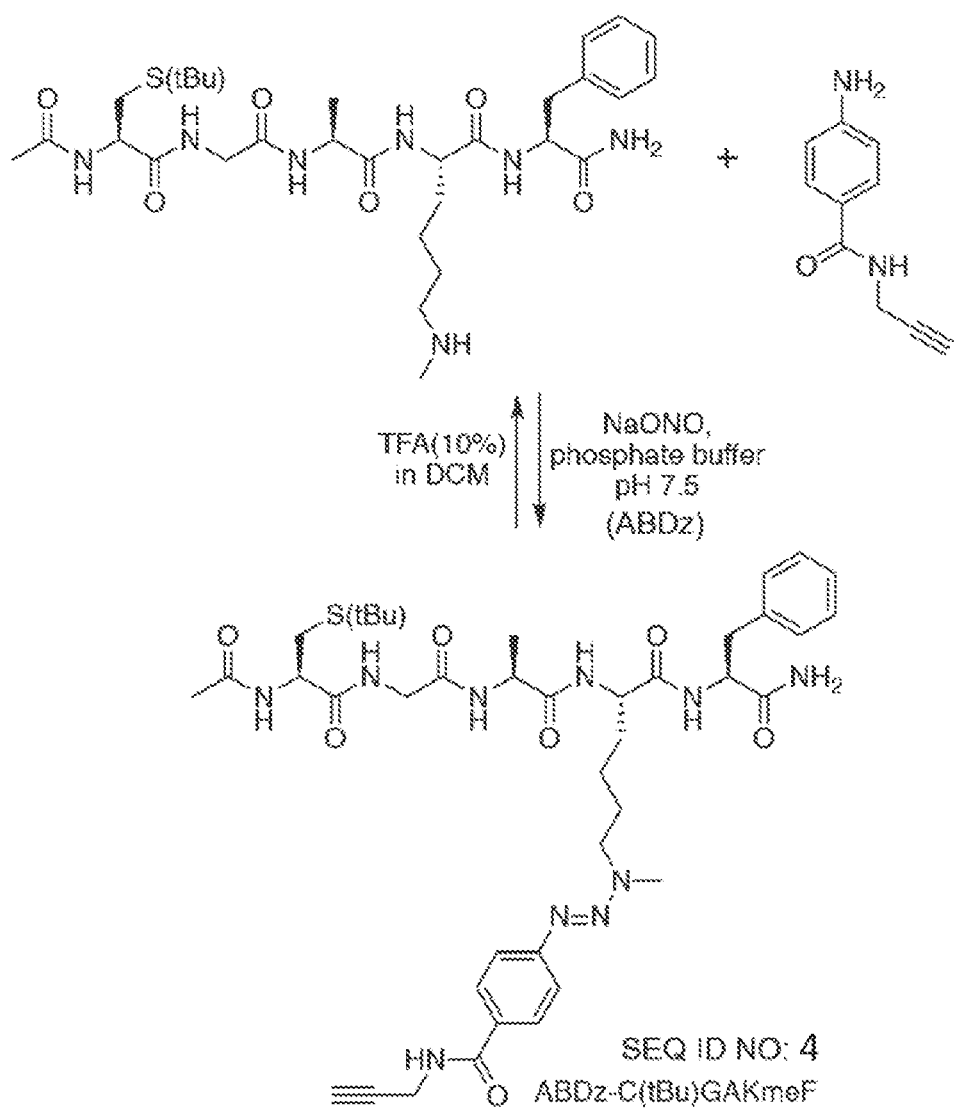
FIG. 4A illustrates the in-situ preparation of an alkyne benzene diazonium (ABDz) and selective reactions with a peptide with a secondary amine, CGAKmeF (SEQ ID NO: 4), which are reversable under acidic conditions providing for a traceless labeling method.

Synthesis of Arene Diazonium Affinity Tags Selective for Monomethyl Lysine and Traceless Enrichment The effective bioconjugation reaction for enrichment should have the ability to attach affinity tags; thus, an alkyne-functionalized aniline was generated. Propargyl amine was coupled to 4-aminobenzoic acid. The alkyne-functionalized aniline [4-amino-N-(prop-2-yn-1yl)benzamide] was thereafter converted to a diazonium ion in situ by treatment with sodium nitrite providing 4-(prop-2-yn-1-ylcarbamoyl)benzenediazonium nitrite [also referred to as the Alkyne-Benzene Diazonium (ABDz)] (FIG. 4A). The ABDz showed high chemoselectivity for monomethyl lysine on reaction with peptides, such as GAKmeF (SEQ ID NO: 3), AKmeF, GGKmeGKF (SEQ ID NO: 5), GKmeAKmeF (SEQ ID NO: 2), and Kme2GGKmeGKF (SEQ ID NO: 6), under optimized conditions (89-95%). Traceless cleavage of triazene-coupling product is accomplished under mild acidic conditions.

Figure 4B:
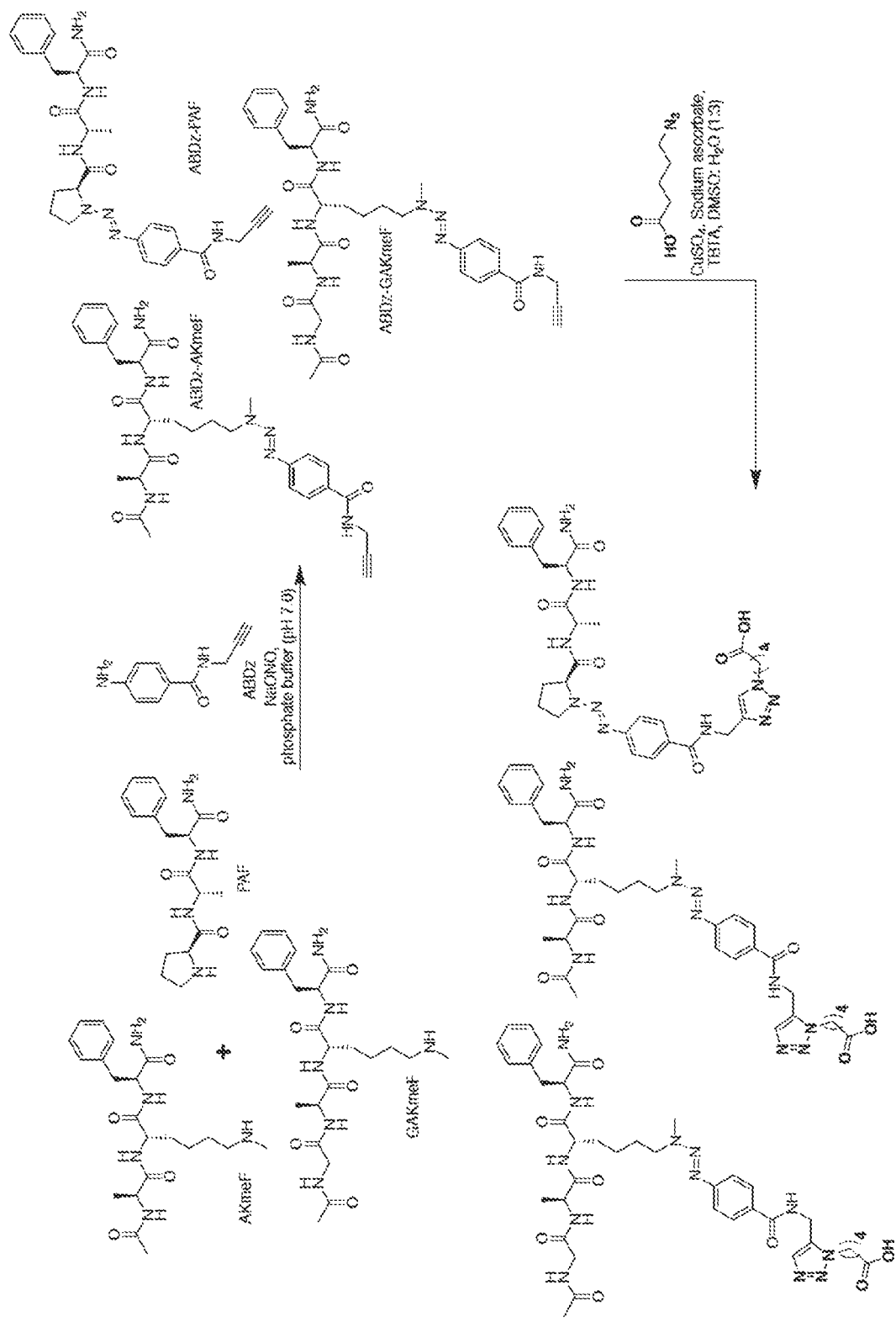
FIG. 4B illustrates a method for selective tagging of peptides with secondary amines in situ by generating a diazonium ion in a complex mixture followed by 2nd functionalization using Click chemistry. A mixture of peptides (1 mg each) including GAKmeF (SEQ ID NO: 3) in 4 mL of 100 mM phosphate buffer (pH 7.0) was added to freshly prepared alkyne functionalized diazonium salt ABDz (4 equiv., 2.4 mM). The solution was stirred at room temperature for 1 h. This was followed by the addition of 5-azidopentonic acid (5 equiv.), $CuSO_4$ (0.1 equiv.), sodium ascorbate (5 equiv), TBTA (0.5 equiv) in 25% of DMSO in water) and the reaction was stirred for 2 h at 40° C. temperature.

As a further demonstration of the high selectivity for monomethyl lysine, multiple peptides were tagged in the same solution in order to test the potential of this method for enrichment in a complex mixture. The mixture of peptides PAF, AKmeF, and GAKmeF (SEQ ID NO: 3) was allowed to react for 1 h under the reaction conditions generating the alkyne benzene diazonium ion ABDz. This was followed by copper (I)-catalyzed alkyne-azide cycloaddition (CuAAC) with 5-azidopentanoic acid in the reaction mixture for 2 h. The reaction products were analyzed by MS and the data indicated tagging with ABDz and enrichment with 5-azidopentanoic acid for all the peptides in the reaction mixture (FIG. 4B).

The chemical stability of the triazene-coupling product was tested under different conditions. The triazene-coupling product acts as a protecting group for secondary amines and tolerates various coupling reagents, such as N,N'-diisopropylcarbodiimide (DIC), and bases, such as N,N-diisopropylethylamine (DIEA) and pyridine (PPR), which is required for Fmoc peptide synthesis. It is also stable to a strong protein disulfide reducing agent tris(2-carboxyethyl) phosphine (TCEP) and click chemistry (CuAAC) conditions. The triazene-linkage showed reasonable stability to sodium dithionate and was stable for 1 h. This is in contrast to the stability of the azo coupling product with Tyr, which degrades quickly in the presence of sodium dithionate to generate modified tyrosine The triazene coupling product 4 MDz-Pro-OMe was incubated in water:ACN mixture for 24 h, and no decomposition of the triazene-coupling product was observed. Even though the triazene-secondary amine linkage is stable under physiologically relevant conditions, experiments were performed to determine whether the conjugate can be decoupled in a traceless manner. Indeed, exposure of the triazene modified peptide 4 MDz-AKmeF to acidic conditions (10% TFA in $H_2O$) led to its rapid cleavage in 5 min to unchanged peptide AKmeF, as observed by HPLC and MS analysis. It is noteworthy that the acidic cleavage generated original coupling partners in an unperturbed manner. In contrast, a handful of the coupling reactions are reversible, but the products derived from decoupling are modified versions of the original reactants. The remarkable speed and selectivity and the ability to subsequently cleave the resulting triazene-linkage in a traceless manner to regenerate the unmodified starting materials, underscores unique advantages of this strategy.

Enrichment of Monomethyl Lysine (Kme) from Complex Mixtures by Solid-Phase Peptide Capture and Release of High-Purity Samples The efficient characterization of monomethyl-lysine-containing peptides from proteolytic fragments is essential, but unfortunately their detection in the complex mixture is highly challenging. One way to selectively trap and detect the monomethyl lysine PTM with high efficiency from the complex mixture is to covalently bind monomethyl lysine peptides directly to the solid support followed by their detachment from the solid support in a traceless manner. There are no known methods available to achieve this goal.

Figure 5:
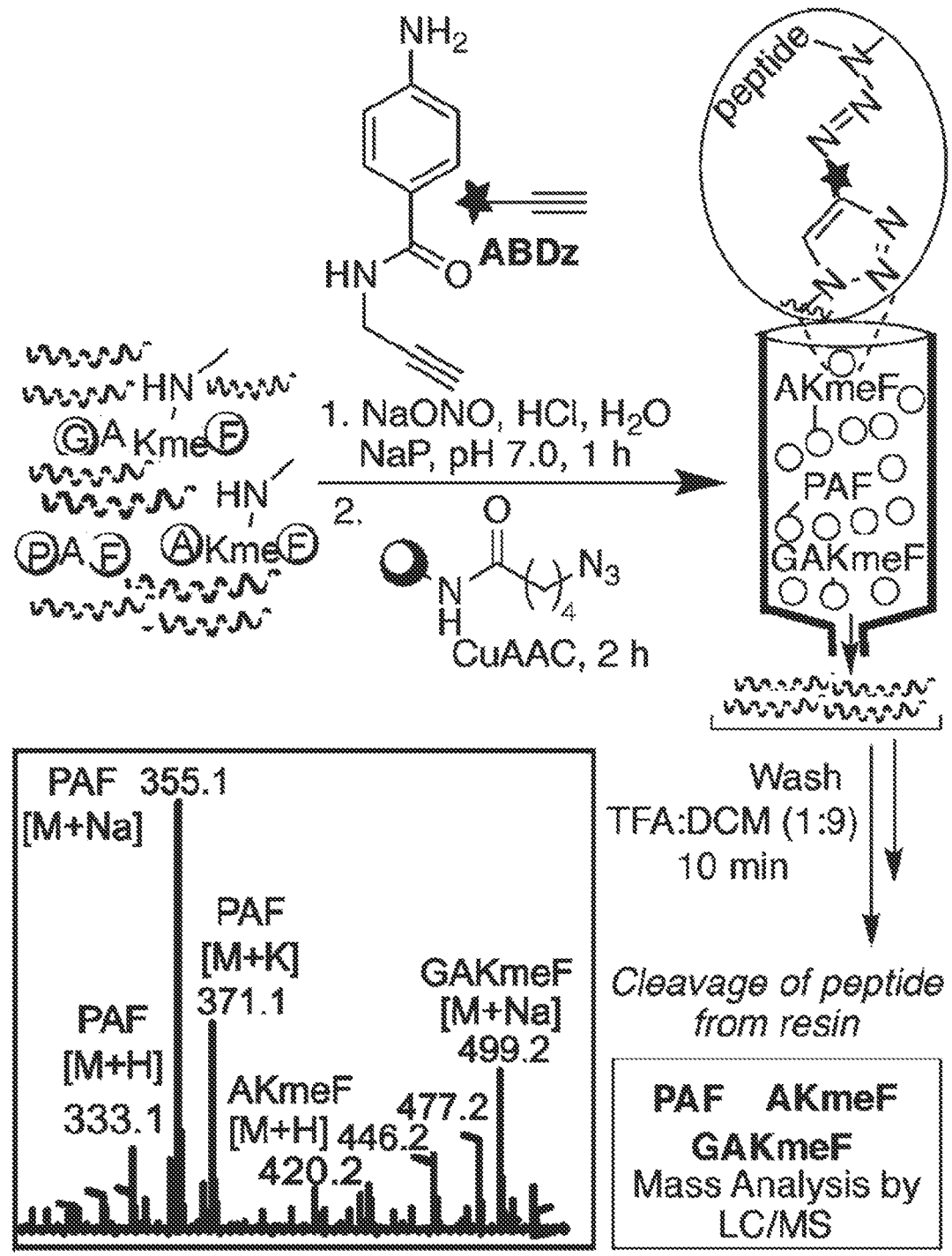
FIG. 5 illustrates site-selective enrichment of secondary amine peptides from a complex mixture. Trypsin digested proteolytic fragments spiked with secondary amine peptides were treated with alkyne-benzene diazonium ion ABDz followed by trapping of triazene-coupling adducts on azide-functionalized beads using click chemistry. The bead trapped peptides were cleavage from the beads under acidic conditions and analyzed using LCMS. Trapping of secondary amine containing peptides including GAKmeF (SEQ ID NO: 3) was confirmed.

A rapid, near quantitative, and site-specific enrichment method of detecting monomethyl lysine peptides from a complex mixture of proteolytic fragments was developed. A trypsin digested proteolytic mixture spiked with various peptides PAF, AKmeF, and GAKmeF (SEQ ID NO: 3) was incubated with ABDz for 1 h, followed by incubation with azide-functionalized resins under click chemistry conditions for 2 h (FIG. 5). The resin was then thoroughly washed with solvents to remove any untrapped proteolytic fragments. The enriched peptides were recovered by cleaving them from resin under acidic conditions (10% TFA in DCM) for 10 min followed by LCMS analysis (FIG. 5). The results showed the capturing of all the peptides containing secondary amines from the complex mixture.

A benzene-diazoniumion-functionalized resin was synthesized in two steps from 5-amino-2-chloro benzylalcohol. The arene-diazonium-ion-functionalized resin was incubated with mixture of peptides AKmeF, SVF, NAF, and RAF containing primary amines and other reactive side chains for 16 h followed by the extensive washing of beads with water and various organic solvents, such as ACN, DMF, MeOH, and DCM, to remove non-covalently attached peptide fragments. The trapped peptides were released from the resin under mild acidic conditions using 10% TFA/DCM for 10 min. High mass intensity of the unmodified monomethyl lysine peptide AKmeF was observed after the cleavage from the resin without any further purification. Peptides without secondary amines SVF, NAF, and RAF were not observed.

Figure 6:
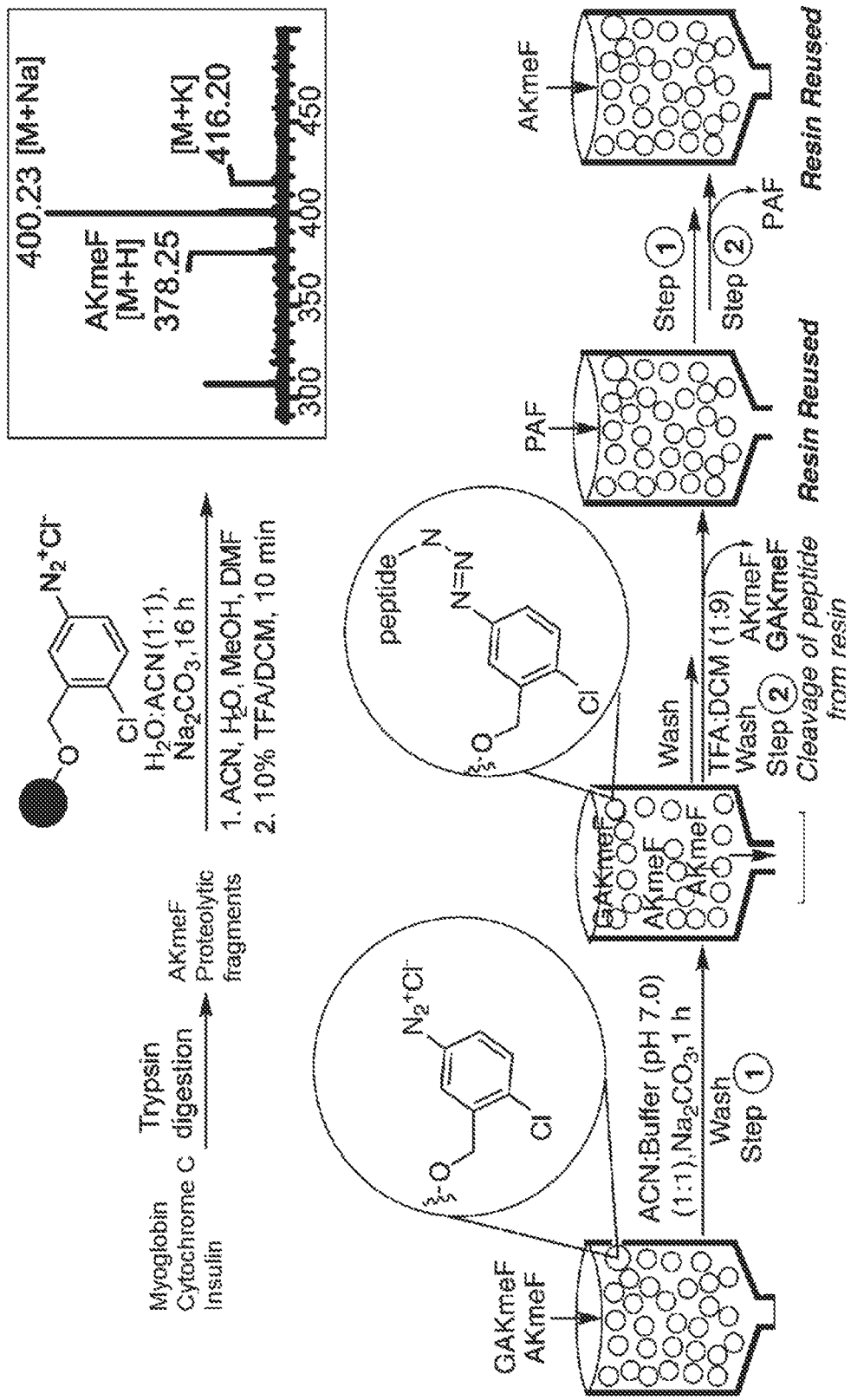
FIG. 6 illustrates selective enrichment of the monomethyl lysine peptides AKmeF, GAKmeF (SEQ ID NO: 3), and proline containing peptides (PAF) from a complex mixture of proteolytic fragments using an arene-diazonium-functionalized solid support, followed by detachment under acidic conditions to release an unmodified peptide as analyzed by MS. Reusability of resin without significant loss of activity was observed. Conditions, peptide (1 equiv), resin (25 equiv), $Na_2CO_3$ (2 equiv/peptide) $H_2O$:ACN (1:1) at room temperature for 16 h incubation. Washing of resin 1 h with ACN, water, MeOH, and DMF. Peptide detachment from resin was accomplished using 10% TFA in DCM for 10 min.

To determine the compatibility of this method in a complex mixture, diazonium-ion-functionalized resin was incubated with trypsin digested protein mixture spiked with monomethylated peptide AKmeF for 16 h followed by excessive washings to remove untrapped peptides from the resin (FIG. 6). The trapped peptides were released under mild conditions (10% TFA/DCM) and unambiguously characterized by MS to confirm the enrichment of AKmeF from a complex mixture. This provides a method to enrich and analyze the monomethyl lysine peptides from a complex mixture by capturing them on a solid support and by reversing it in a traceless manner to release highly pure, unmodified peptides.

Since the acidic cleavage regenerates the unmodified diazonium-ion-functionalized resin, the resin was reused again to capture another set of monomethyl lysine peptide fragments. The diazonium-ion-functionalized resin was incubated with peptides AKmeF and GAKmeF (SEQ ID NO: 3) and $Na_2CO_3$ for 1 h followed by washing and detachment under mild acidic conditions (10% TFA in DCM in 10 min). The MS analysis confirmed the attachment of both AKmeF and GAKmeF (SEQ ID NO: 3) peptides on the resin. This was followed by the incubation of the cleaved resin with another peptide PAF to avoid any kind of false results due to the first peptide capturing. Again, MS analysis after decoupling confirmed the attachment of PAF peptide on the resin. This process was repeated a third time with a peptide, AKmeF. The enrichment of the secondary amine peptide was observed using the same resin.

Next, the peptide trapping was determined in a quantitative manner by incubating peptides (NHMe)AVF and GAK-meF (SEQ ID NO: 3) with the arene-diazonium ion resin followed by measuring the reduction in the peptide concentration in solution using anisole as standard over a 2 h period at room temperature using LCMS. The results indicated the trapping of 56% of peptides in 1 h and 87% of peptides in 2 h.

Figure 7:
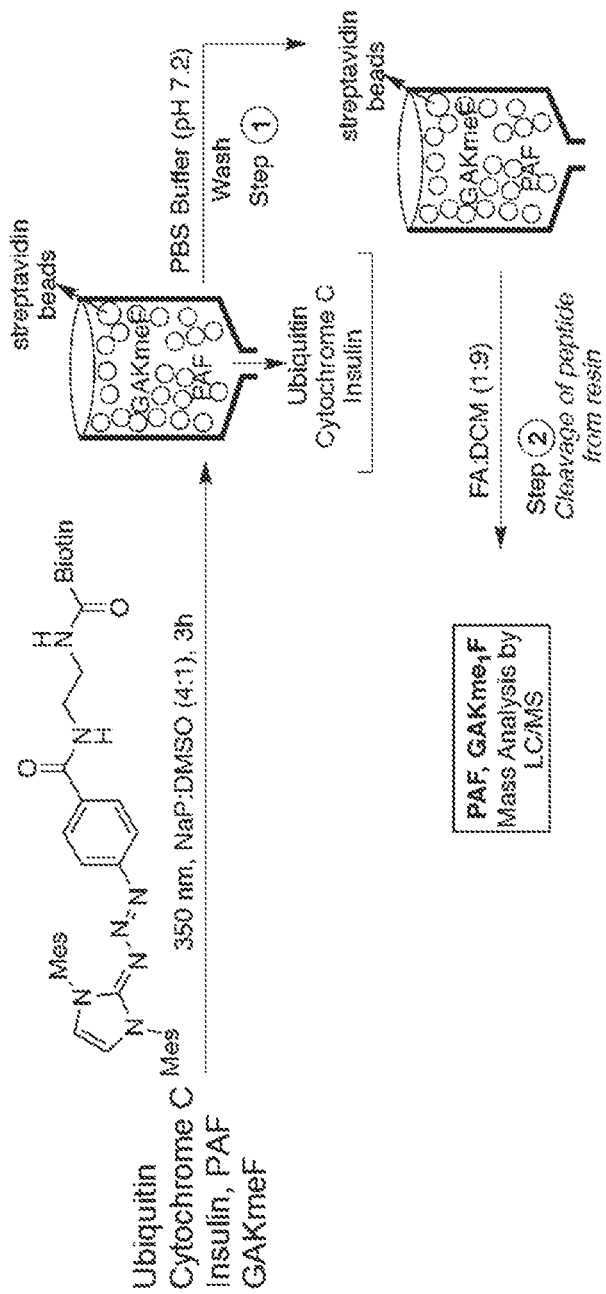
FIG. 7 illustrates enrichment of secondary amine fragments from a complex mixture using a biotin probe and streptavidin beads. Myoglobin (58 uM), cytochrome C (40 uM) and insulin (86 uM) were dissolved in sodium phosphate buffer, 0.1 M pH 7.5. To the mixture, 1 mg each of PAF (500 uM) and GAKmeF (SEQ ID NO: 3) (349 uM) were added to the protein mixture. A biotin functionalized probe 5 mg was dissolved in DMSO and buffer (0.1 M pH 7.5) and added to the protein mixture-total volume: 6 mL (80% buffer (0.1 M pH 7.5): 20% DMSO). The reaction was initiated with 350 nm of light 1 hr to release the free diazonium group and left to stir at RT for 3 hours. The reaction mixture was lyophilized to remove DMSO and streptavidin resin was used to enrich the biotin tagged fragments from a complex mixture. Formic acid (10%) (FA) in DCM was added to the resin for 30 mins to release the enriched peptides, followed by removal of solvent. Released peptides were monitored/analyzed by LCMS.
Figure 8:
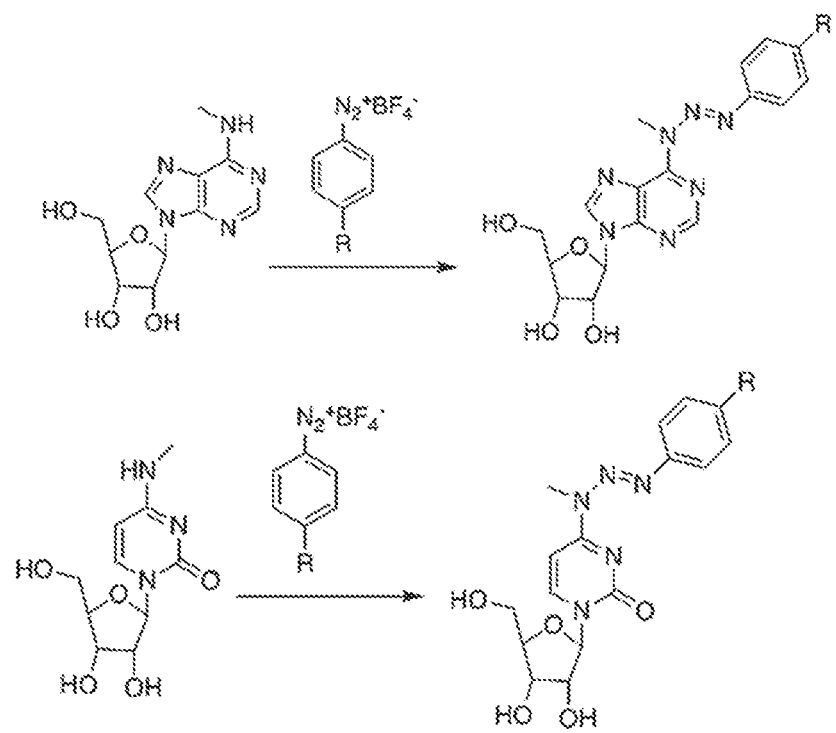
FIG. 8 illustrates the methylation of $N^6$-methyl adenosine and $N^4$-methyl cytosine.

Experiments were performed to determine whether one can enrich secondary-amine-containing peptides from a complex mixture of proteins using a biotin-functionalized probe followed by streptavidin enrichment (FIG. 7). The trapped peptides were released in a traceless manner under acidic conditions from streptavidin beads and the reaction was analyzed by LCMS. The results indicated that secondary-amine-containing peptides were enriched selectively from a complex mixture.

---

SEQUENCE LISTING

```
Sequence total quantity: 6
SEQ ID NO: 1            moltype = AA  length = 15
FEATURE                 Location/Qualifiers
source                  1..15
                        mol_type = protein
                        organism = synthetic construct
SEQUENCE: 1
GEPGIAGFKG EQGPK                                                          15

SEQ ID NO: 2            moltype = AA  length = 5
FEATURE                 Location/Qualifiers
source                  1..5
                        mol_type = protein
                        organism = synthetic construct
SEQUENCE: 2
GKAKF                                                                      5

SEQ ID NO: 3            moltype = AA  length = 4
FEATURE                 Location/Qualifiers
source                  1..4
                        mol_type = protein
                        organism = synthetic construct
SEQUENCE: 3
GAKF                                                                       4

SEQ ID NO: 4            moltype = AA  length = 5
FEATURE                 Location/Qualifiers
source                  1..5
                        mol_type = protein
                        organism = synthetic construct
SEQUENCE: 4
CGAKF                                                                      5

SEQ ID NO: 5            moltype = AA  length = 6
FEATURE                 Location/Qualifiers
source                  1..6
                        mol_type = protein
                        organism = synthetic construct
SEQUENCE: 5
GGKGKF                                                                     6

SEQ ID NO: 6            moltype = AA  length = 7
FEATURE                 Location/Qualifiers
source                  1..7
                        mol_type = protein
                        organism = synthetic construct
SEQUENCE: 6
KGGKGKF                                                                    7
```

The invention claimed is:

1. A method of forming a triazene labeled peptide or nucleic acid comprising contacting a peptide or nucleic acid comprising a secondary amine group and a primarily amine group with a compound comprising an aromatic group with a diazonium para substituted with an electron rich group under conditions providing a triazene labeled peptide or nucleic acid formed at the secondary amine group;

wherein a triazene labeled peptide is not formed at the primary amine group; and wherein the conditions providing a triazene labeled peptide or nucleic acid are in an aqueous solution with a pH of between 6.5 to 7.5.

2. The method of claim 1, wherein the peptide comprising a secondary amine group is a peptide comprising $N^6$-methyl-lysine.

3. The method of claim 1, wherein the peptide comprising a secondary amine group is a peptide comprising an N-terminal proline.

4. The method of claim 1, wherein the nucleic acid comprising a secondary amine group is DNA or RNA comprising $N^6$-methyl adenosine or $N^4$-methyl cytosine.

5. The method of claim 1, wherein the compound comprising an aromatic group with a diazonium substituent para substituted with an electron rich group has the following formula,

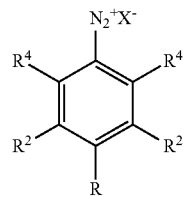

or derivatives thereof, wherein

R is an electron rich group optionally substituted or conjugated to a label or a solid support through a linking group;

$R^2$ and $R^4$ are individually and independently at each occurrence hydrogen or alkyl, wherein $R^2$ and $R^4$ are optionally substituted; or $R^2$ or $R^4$ and the attached atoms together form an aromatic or non-aromatic ring optionally substituted; and $X^-$ is a counter anion.

6. The method of claim 5, wherein R is a halogen, alkoxy, alkylthio, dialkylamino, acetamido, formyl, carboxyl, carbamoyl, or N-substituted carbamoyl group wherein R is optionally substituted with one or more substituents.

7. The method of claim 5, wherein R is substituted with a linking group comprising an alkynyl group or R is —C=$ONR^1$, wherein $R^1$ is an alkynyl group.

8. The method of claim 1, wherein the diazonium para substituted with an electron rich group is formed by the process of contacting 4-amino-N-(alkynyl)benzamide, a nitrite salt, and a phosphate salt at pH of between 6.5 to 7.5.

* * * * *